(12) United States Patent
Cree

(10) Patent No.: US 11,813,424 B1
(45) Date of Patent: Nov. 14, 2023

(54) INLINE INJECTION PORT ASSEMBLY

(71) Applicant: PMT Corporation, Chanhassen, MN (US)

(72) Inventor: Matthew W Cree, Victoria, MN (US)

(73) Assignee: PMT Corporation, Chanhassen, MN (US)

( * ) Notice: Subject to any disclaimer, the term of this patent is extended or adjusted under 35 U.S.C. 154(b) by 540 days.

(21) Appl. No.: 16/673,187

(22) Filed: Nov. 4, 2019

Related U.S. Application Data

(60) Provisional application No. 62/756,688, filed on Nov. 7, 2018.

(51) Int. Cl.
*A61M 39/02* (2006.01)
*A61M 39/04* (2006.01)
*A61B 90/00* (2016.01)

(52) U.S. Cl.
CPC ......... *A61M 39/0247* (2013.01); *A61B 90/02* (2016.02); *A61M 39/04* (2013.01); *A61M 2039/0205* (2013.01); *A61M 2039/0282* (2013.01); *A61M 2039/0288* (2013.01)

(58) Field of Classification Search
CPC .......... A61M 39/0208; A61M 39/0247; A61M 39/04; A61M 2039/0205; A61M 2039/0282; A61M 2039/0288; A61M 39/02; A61M 39/0223; A61M 2039/0229; A61M 2039/0261; A61M 2039/0279; A61M 2039/0273; A61M 2039/027; A61M 2039/0276; A61B 90/02
See application file for complete search history.

(56) References Cited

U.S. PATENT DOCUMENTS

| | | | |
|---|---|---|---|
| 4,915,690 A | 4/1990 | Cone et al. | |
| 5,108,377 A | 4/1992 | Cone et al. | |
| 5,848,989 A * | 12/1998 | Villani | A61M 39/0208 604/288.02 |
| 2008/0009809 A1* | 1/2008 | Guala | A61M 39/04 604/246 |
| 2011/0218392 A1* | 9/2011 | Honaryar | A61M 39/0208 600/37 |

* cited by examiner

*Primary Examiner* — Lauren P Farrar
*Assistant Examiner* — Hamza A Darb
(74) *Attorney, Agent, or Firm* — Eggink & Eggink; Anthony G. Eggink; Katrina M. Eggink

(57) ABSTRACT

An inline injection port assembly having a rigid tubular port body with a cap structure mounted thereto and a barbed tubing connector extending from the opposite end thereof. The cap structure has to a self-sealing elastomeric injection structure which extends into the port body and which is held in a compressed state therein. The cap structure and the barbed tubing connector are axially aligned to thereby provide a low profile inline injection port assembly.

17 Claims, 4 Drawing Sheets

INLINE INJECTION PORT ASSEMBLY

This application claims the benefit of U.S. Provisional Patent Application No. 62/756,688, filed on Nov. 7, 2018, the disclosure of which is incorporated by reference in its entirety.

The present invention relates generally to an injection port fin an implanted tissue expander device, for example. Particularly, the invention relates to an improved inline injection port assembly having a tubular port body with an aligned barbed tubing connector and an aligned cap structure having a self-sealing injection area to thereby provide a low profile inline injection port assembly.

Although injection ports for tissue expanders are known, prior art injection ports typically have various limitations and shortcomings. For example, prior art tissue expander implants typically utilize a dual barb tubing connector for attachment to the tissue expander tubing and to the injection port tubing. A surgeon is therefore required to suture both the tissue expander tubing and the injection port tubing to the dual barb connector. The inline injection port assembly of the present invention requires the surgeon to only suture the port assembly to the tissue expander tubing.

Prior art injection ports are also generally flat in structure and the tubing and/or saline exits from the edge or from the outside diameter of the injection area. The saline flow is therefore required to change directions by 90 degrees within these prior art port structures. In the present invention, the saline solution exits the inline port assembly parallel or in alignment with the fill tubing thereby allowing the outside diameter of the port assembly to be greatly reduced in size and improving fluid flow. The low profile assembly structure also increases the possible applications of the inline injection port structure.

Prior art injection ports also typically require a needle stop plate structure to restrict the penetration of the hypodermic needle utilized for filling the port body with a fluid. The inline injection port assembly of the present invention has a structure which does not require a needle stop plate and which further provides for efficient fluid flow.

In summary, the inline injection port assembly of the invention reduces the size and complexity of an injection port device and simplifies the use of remotely located injection ports which are used to fill tissue expander implants with a fluid such as saline, for example. A barbed tubing connector is integrated into the injection port structure and the inline injection port is constructed to self seal after multiple injections with a hypodermic needle.

SUMMARY OF THE INVENTION

A low profile injection port assembly having a rigid tubular body with a barbed tubing connector extending from one end and an axially aligned elastomeric cap structure mounted at the opposite end. The elastomeric cap structure has an injection area and a downwardly extending cylindrical portion and may be comprised of an elastomer such as a compressed silicone rubber, for example.

The tubular cup body of the inline injection port assembly integrates the rigid barb tubing connector and also compresses the cylindrical portion of the cap structure thereby allowing for multiple injections with a hypodermic needle. The inside diameter of the barb connection drafts smaller than the outside diameter of the recommended filling needle. The composition of the rigid port body structure and the inside diameter design eliminates the possibility of the needle puncturing straight thru the port body and also eliminates the need for a needle stopping plate utilized in prior art tissue expander injection ports. The inline injection port may be directly sutured onto the tissue expander tubing, thereby eliminating the dual barb tubing connector and the need to suture two pieces of tubing together.

The inline injection port assembly further provides a rigid tubular port structure with a formed cavity having a structure that results in optimal fluid flow to the barbed tubing connector.

An advantage of the invention is that the low profile structure of the inline injection port assembly allows the overall size of the injection port to be reduced, thus allowing the injection port to fit in smaller areas of the body, such as within the oral cavity, for example. The inline injection port may also be beneficial for pediatric tissue expansion surgeries, where the injection ports are not intended to be implanted and are routinely placed external to the implant pocket to aid in patient compliance. The remotely located injection ports for pediatric tissue expanders are routinely not implanted and the tubing is allowed to exit the implant pocket, so multiple injections can be performed without requiring medical staff to inject a child with a needle, for example. The reduced size of the inline injection port of the present invention improves the per of pediatric tissue expansion cases by making the port easier to cover with a bandage and to avoid getting damaged by external forces.

Another advantage of the invention is that the inline injection port assembly may be beneficial for treating chemotherapy patients. The discrete size and inherent simplicity of the injection port design, and structure benefits patients requiring multiple injections or those that are connected intravenously to medication by reducing the number of skin punctures.

These and other advantages of this invention will become clear from the following description by reference to the drawings.

DESCRIPTION OF THE PREFERRED EMBODIMENTS

Figure 1:
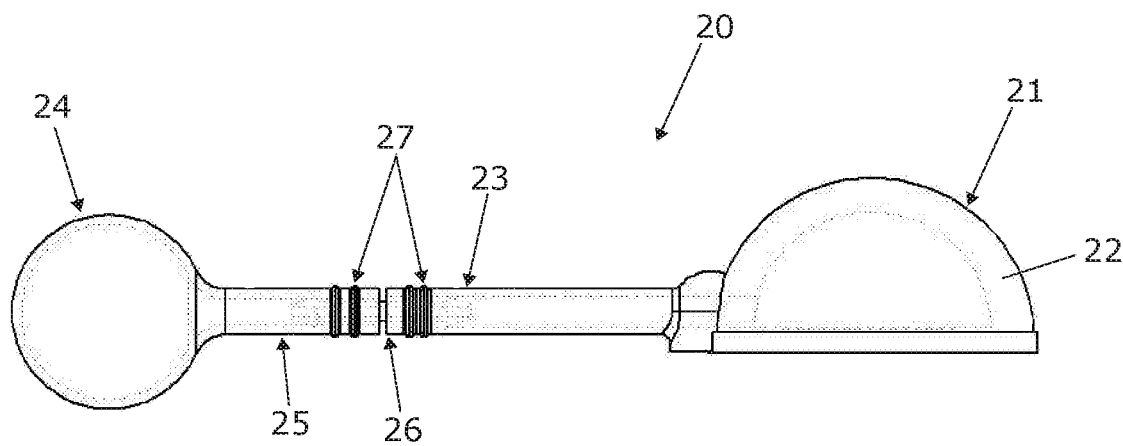
FIG. 1 is a lateral plan view of a prior art tissue expander implant assembled with a remotely located injection port.
Figure 2:
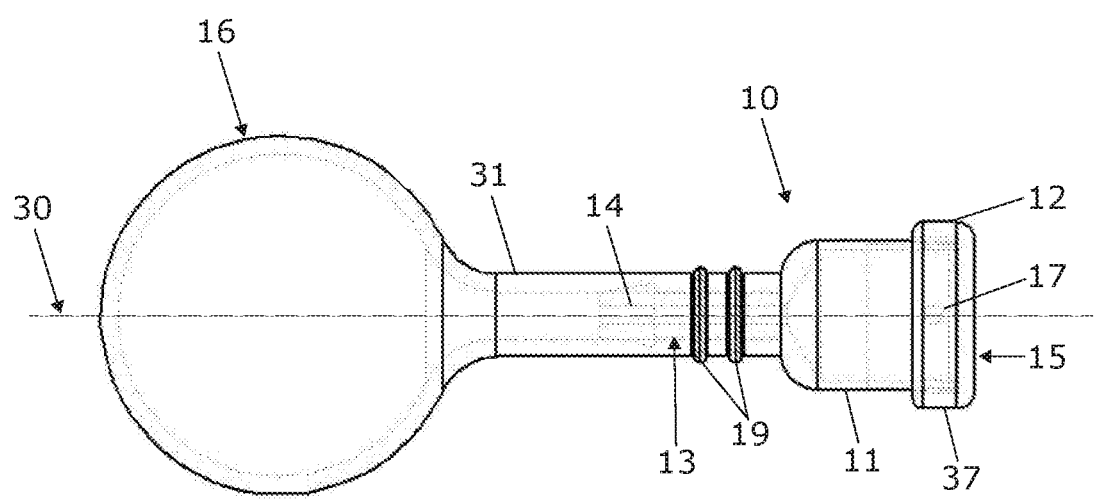
FIG. 2 is a lateral plan view of the inline injection port assembly of the present invention assembled with a tissue expander implant.
Figure 3:
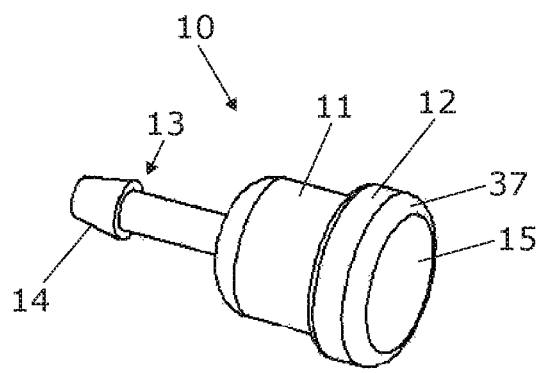
FIG. 3 is a perspective view of the inline injection port of the invention.

FIG. 1 is a lateral view of a prior art tissue expander implant having a remotely located injection port assembly 20. As shown, the tissue expander 24 is connected to the injection port body 22 by means of till tubing 25 and 23 which are interconnected by dual barbed connector 26 and held together by sutures 27 on each end of the dual barbed connector 26. The injection port 22 has an injection area 21 which is spatially parallel fill tubing 23 and 25 thereby requiring an injected fluid to travel at a 90 degree angle when introduced into the injection port body 22. The injection port body 22 further has an injection needle stop plate (not shown) which prevents damage to the port body 22 which may result during the fluid filling process.

Referring to FIGS. 2-5, the inline injection port assembly 10 of the present invention is shown having a unitary tubular port body or cup structure 11 having a barbed tubing connector 13 extending from one end thereof. A cap structure 12 is shown secured to the opposite of the port body 11. The cap structure 12 is shown having a bottom projection 18 and self-sealing injection area 15. A tissue expander 16 is shown connected to the barbed tubing connector 13 by means of fill tubing 31. The till tubing 31 is shown secured over barbed end 14 and to tubing connector 13 by means of sutures 19. The various elements are shown aligned with respect to axis 30.

Figure 5:
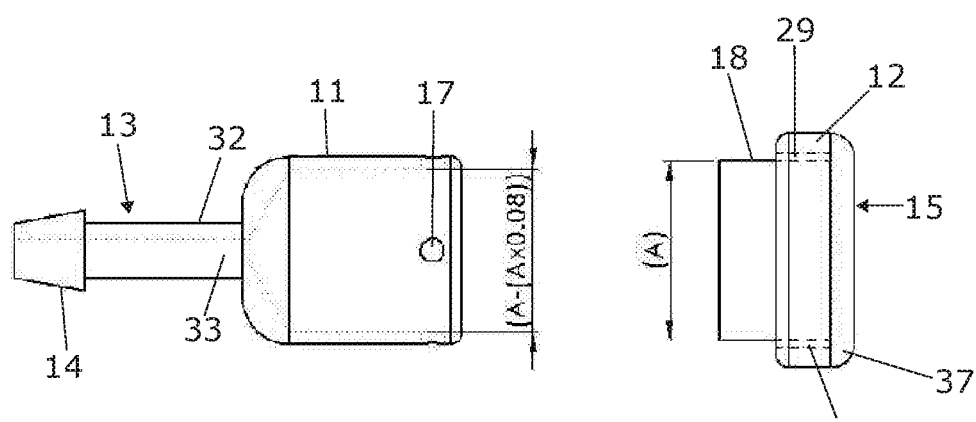
FIG. 5 is a lateral plan view of the inline injection port assembly and showing the cup body and cap structure.

The cap structure 12 is shown having a rounded peripheral edge 37 with an uncompressed outside diameter defining the generally flat injection area 15 and which is formed of an elastomer such as silicone rubber, for example. As shown in FIG. 5, the diameter of the cylindrical portion 18 of the cap structure is larger than the inside diameter of barbed connector cup 11 to thereby apply enough compressional forces equally around the cylindrical portion 18 to make the silicone rubber effectively self-seal after being punctured by a hypodermic needle. The comparative ratio between these two diameters may vary depending on the required needle size. For example, in order for the inline port to effectively self-seal after being punctured by 21 gauge or smaller needle, the preferable difference from the inside of the port diameter may be 8% less with respect to the outside diameter of the cylindrical portion 18 of the cap structure 12, as shown in FIG. 5, however this dimension may be modified without changing the purview of this invention. For example, the compression of the elastomer may range between 5-15%. The optimal silicone rubber durometer for the injection area 15 to allow for the self-sealing characteristics may be 30A shore (±20A shore). The unitary cap structure 12 having injection area 15 and cylindrical portion 18 is further held within the top portion of cup 11 by means of a silicone adhesive, for example, as further described below.

Figure 6:
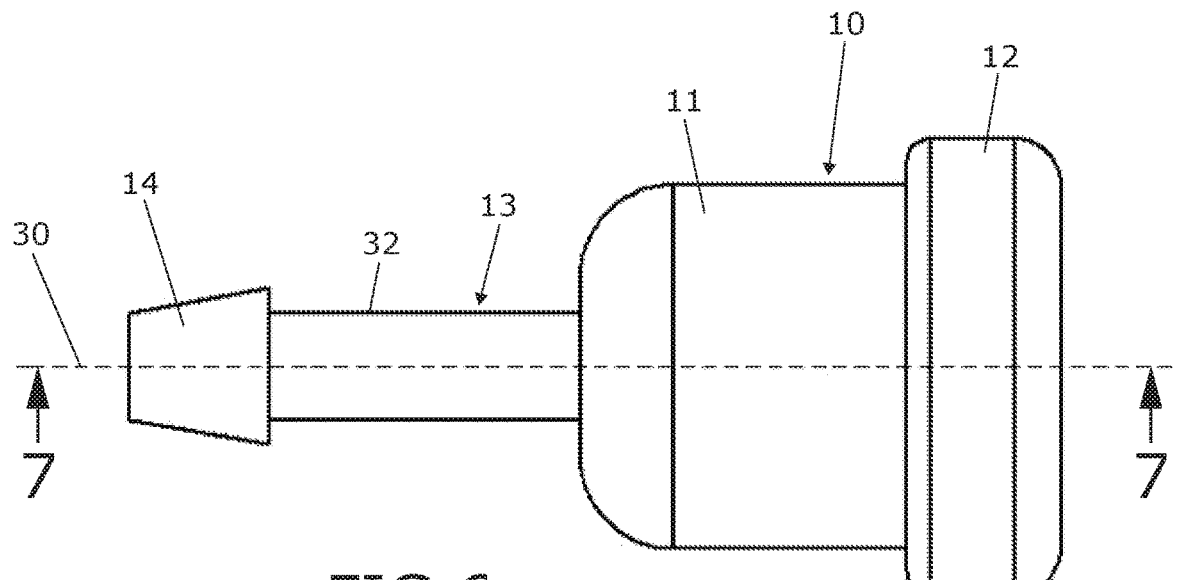
FIG. 6 is a lateral plan view of the injection port assembly.
Figure 7:
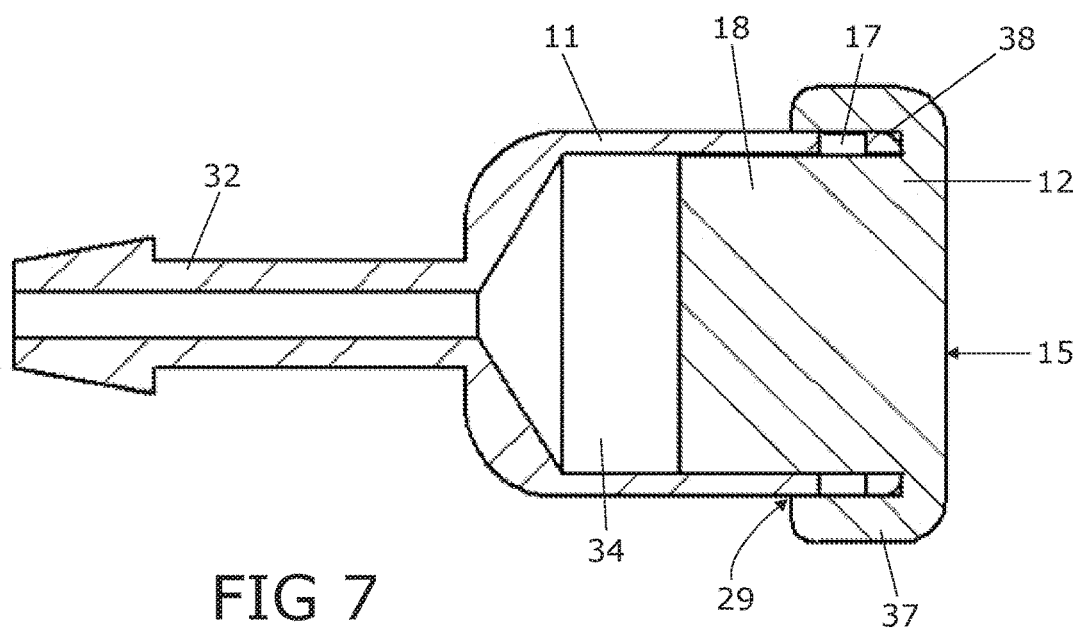
FIG. 7 is a sectional view taken along lines 7 of FIG. 6 and showing the pun body and cap structure of the injection port assembly.

As shown in FIGS. 6 and 7, the port body or connector cup body 11 is a unitary structure having an upper portion with a tubular open top and a plurality of holes or apertures 17. The cap structure 12 is shown as a unitary structure having a rounded upper peripheral edge 37 and a depending cylindrical bottom portion 18 with a circumferential groove or slot 29 at the top of portion 18 which is constructed and arranged to receive the upper portion of the port body 11. The port body 11 and the cap 12 are joined and sealed together by means of an adhesive 38, i.e., a silicone adhesive which is applied in the circumferential slot 29 and which permits the adhesive to extend through securing holes 17 to thereby adhere and seal the cap structure 12 to the cup body 11. The self-sealing elastomeric cylindrical structure 18 is held under compression within the upper portion of port body 11 and is shown accessible at the injection area 15 of the cap structure 12.

In order to provide a self-sealing structure, the injection area 15 of the inline port assembly 10 is preferably formed of a biocompatible elastomer, such as a silicone rubber. The self-sealing injection area 15 may be constructed of other types of rubber; however, natural rubber or latex may result in an adverse reaction for the patient, if they have allergies to these materials.

Figure 8:
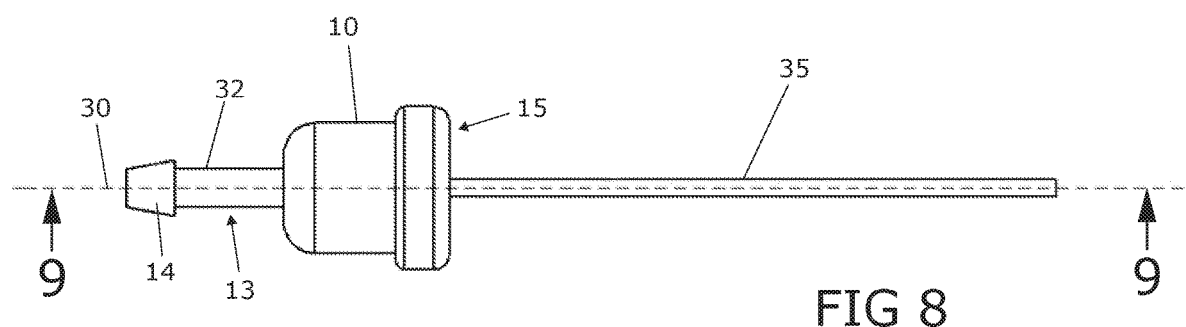
FIG. 8 is a lateral view showing a filling needle inserted into the inline injection port assembly.
Figure 9:
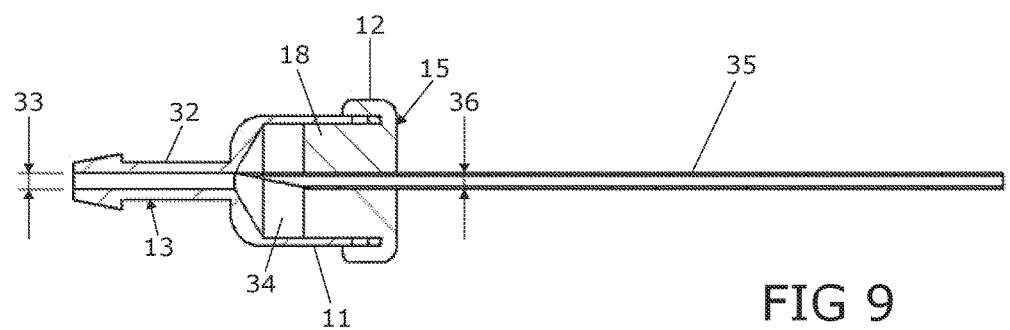
FIG. 9 is a sectional view taken along lines 9-9 of FIG. 8.

As shown in FIGS. 8 and 9, the fluid release chamber 34 of port body 11 is funnel shaped and allows enough of the injection needle 35 to be exposed from the silicone injection area 15 to insure that fluid can exit the injection needle into the tubular outlet 32 without being restricted. The required depth of the fluid release chamber of port body 11 is preferably at least 0.080 inches to accommodate a 21 gauge or smaller filling needle, for example.

As further shown in FIG. 9, the inside diameter 33 of the barbed connector 13 is smaller than the outside diameter 36 of the intended filling needle 35 that is utilized for fluid filling purposes to thereby prevent the tilling needle 35 from puncturing through the barbed connector 13 and damaging the tissue expander tubing 31.

Regarding the manufacture and assembly of the inline injection port assembly 10, the silicone injection cap 12 may be formed by applying heat and pressure to vulcanize liquid silicone resin within a mold and the barbed connector cup or port body 11 may be machined from stainless steel or other implant grade material, as further set forth below.

The injection cap 12 is inserted and adhered to the cup body 11 using a silicone adhesive, for example. The silicone adhesive 38 is applied to the peripheral silicone cap groove or slot 29, as shown in FIGS. 5 and 7, and is able to flow through the cap securing holes 17 around the periphery of the port body 11 and to the projection 18 of cap structure 12. After the adhesive 38 is cured, it bonds to both the inside and outside of the cup of body 11 of the barbed connector, as well as thru the cap securing holes 17, thereby adhering and sealing the silicone injection cap 12 to the port body 11. The inline port assembly 10 may be is packaged in sealed Tyvek pouch and sterilized for single use.

Figure 4:
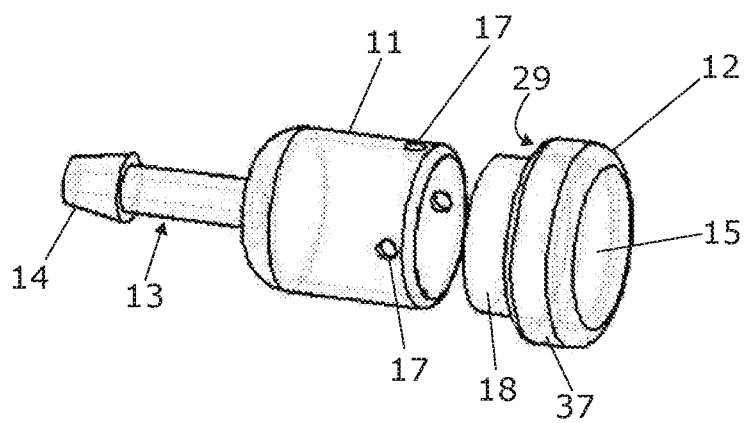
FIG. 4 is a perspective view of the inline injection port of FIG. 3 and shown in a disassembled state.

In summary and referring particularly to FIGS. 4, 5, and 7, the inline port assembly 10 of the invention is a two part structure, comprising a rigid port body 11 and an elastomeric cap structure 12. The elastomeric cap structure 12 has a continuous top surface 15 and circumferential slot 29 spaced from the top surface 15 and adjacent the self sealing cylindrical bottom portion 18 which is held under compression within the upper portion of the rigid port body 11. A plurality of apertures 17 in the upper portion of the port body 11 allow adhesive within the circumferential slot 29 to bond or seal the cap structure 12 to both the inside and outside surfaces of the cylindrical port body 11. The port body 11 is configured to hold the cylindrical bottom portion 18 of the cap structure 12 in a predetermined state of compression as further discussed herein. As shown in FIG. 7, the port body 11 has a fluid release chamber 34 below the compressed bottom portion 18 and which tapers into the tubular outlet 32 of the barbed connector 13. The rigid port body 11 is constructed and arranged to not require a needle guard structure.

Other medical grade materials that may be utilized in the invention include, for example, Aluminum, Titanium, Polyether ether ketone (PEEK), High-density polyethylene (HDPE), Polyurethane, Polytetrafluoroethylene (PTFE), Acrylic, Polystyrene and Polyvinyl chloride (PVC).

The port body 11 and barbed connector 13 could be machined, mental injection molded or three dimensionally printed from Titanium, to allow the inline injection port assembly 10 to be conditionally safe to be scanned by a Magnetic resonance imaging (MRI) up to 3 Tesla and would be radiopaque to X-ray scans. The inline injection port assembly 10 could also be cut, injection molded or three dimensionally printed from a plastic resin, such as Polyether ether ketone (PEEK), to thereby allow the inline injection assembly port assembly to be completely MRI safe and radiolucent to X-ray scans.

In summary, the inline injection port assembly 10 is generally a two piece design comprised of a unitary and rigid barbed tubing connector extending from a tubular port body 11 and a unitary elastomer cap structure 12. The self-sealing silicone injection elastomer 18 of the cap structure 12 is compressed by the connector cup 11. This simple and efficient design saves time in manufacturing, assembly and eliminates the need for multiple silicone molds.

The inside diameter of the barbed connector 13 is preferably larger than the inside diameter of the intended filling needle to ensure the fluid flow rate is not restricted. The fluid flow rate is limited by the smallest diameter within the fluid path. The injection port performance is essentially dependent on the ease of fluid transfer thru the port body and any flow restriction is undesirable.

As many changes are possible to the inline injection port embodiments of this invention utilizing the teachings thereof, the description above, and the accompanying drawing should be interpreted in the illustrative and not in the hunted sense.

That which is claimed is:

1. A two piece inline injection port assembly comprising:
a) a unitary rigid tubular port body having opposing ends;
b) a barbed tubing connector extending from one end;
c) a unitary elastomeric cap structure secured to the opposite end of said rigid tubular port body, said unitary cap structure having a cylindrical upper portion with a continuous, planar top surface and a self-sealing elastomeric body, said unitary elastomeric cap structure having a compressed cylindrical portion spaced from and extending downwardly from said planar top surface of said cylindrical upper portion and into said rigid, unitary tubular port body;
d) said unitary, rigid tubular port body having an open funnel shaped fluid release chamber spaced from an extending below said compressed cylindrical portion at least 0.080 inches; said funnel shaped chamber terminating at said barbed tubing connector;
e) said opposite end of said rigid tubular port body having an inside diameter adapted to maintain said compressed cylindrical portion of said cap structure in a predetermined state of compression between 5 and 15% and wherein said elastomeric cap structure has a hardness of 30A Shore±20A Shore; and
f) wherein said tubular port body has an upper portion and wherein said elastomeric cap structure has a peripheral edge and an interiorly disposed circumferential slot spaced from said peripheral edge and adjacent said compressed cylindrical portion to thereby receive said upper portion of said tubular port body, said circumferential slot spaced downwardly from said continuous, planar top surface of said unitary, elastomeric cap structure and wherein said upper portion of said unitary rigid tubular port body has a plurality of apertures for securing and sealing said unitary cap structure thereto within said circumferential slot of said unitary cap structure, whereby said tubular port body and said unitary cap structure are sealed on both the inner and outer sides of said tubular port body.

2. The two piece inline injection port assembly of claim 1, wherein said self-sealing body is comprised of a silicone rubber and wherein said unitary tubular port body is formed of a stainless steel.

3. The two piece inline injection port assembly of claim 1, wherein said barbed tubing connector has an inside diameter smaller than the outside diameter of a hypodermic needle utilized to till said injection port assembly, whereby said injection port assembly does not require a needle guard within said fluid release chamber.

4. The two piece inline injection port assembly of claim 1, wherein said unitary rigid tubular port body is constructed of a material selected from the group of materials consisting of stainless steel, titanium, PEEK, HDPE, PVC, Polystyrene, Aluminum, Polyurethane, PTFE and Acrylic.

5. An inline injection port assembly comprising:
a. a unitary tubular body having a circumferential wall with inner and outer surfaces, a top portion and a bottom portion with a funnel shaped fluid release chamber, said top portion having a top opening and said circumferential wall having a plurality of spaced openings adjacent said open top;
b. a unitary, elastomeric cap structure baying a cylindrical top portion with a planar top surface and a bottom cylindrical projection being unitary with and downwardly extending therefrom and spaced perpendicularly from said planar top surface, a circumferential channel adjacent said bottom cylindrical projection and extending into said tap cylindrical portion of said unitary cap structure, said circumferential channel being constructed and arranged to receive said top portion of said unitary tubular body and covering said plurality of openings of said unitary tubular body, said bottom cylindrical projection being compressingly held in said top portion of said rigid tubular body;
c. adhesive within said circumferential channel and protruding through said plurality of openings of said tubular body to sealingly adhere said unitary elastomeric rigid cap structure to said unitary tubular body, whereby said cap structure and said tubular body are sealingly bonded on both the inner and outer surfaces of said circumferential wail of said tubular body; and
d. a conduit extending from said funnel shaped fluid release chamber at a distance of at least 0.080 inches from said cylindrical projection of said cap structure, said conduit having a barbed terminal end and being axially aligned with said tubular body and said unitary cap structure.

6. The inline injection port body of claim 5, wherein said conduit extending from said funnel shaped fluid release chamber of said bottom portion has an inside first diameter and wherein a syringe is provided having an outside second diameter, said first diameter being smaller than said second diameter, whereby said inline injection port body is constructed and arranged to not require a needle guard member.

7. The inline injection port body of claim 5, wherein said bottom projection of said cap structure a radially compressed between 5 and 15% and wherein said elastomer has a hardness of 30A Shore±20A Shore.

8. The inline injection port assembly of claim 7, wherein said conduit extending from said funnel shaped fluid release chamber has an inside diameter smaller than the outside diameter of a hypodermic needle utilized to fill said injection port assembly to thereby eliminate the need for a needle guard structure.

9. The inline injection port body of claim 5, wherein said elastomer is a silicone rubber.

10. The inline injection port body of claim 5, wherein said tubular body is constructed of a material selected from the group of materials consisting of stainless steel, titanium, PEEK, HPDE, PVC, Polystyrene, Aluminum, Polyurethane, PTFE , and Acrylic.

11. The inline injection port assembly of 5, wherein said injection port assembly is a two piece structure.

12. A two piece low profile inline injection port assembly comprising a unitary cylindrical and rigid injection port body having a unitary elastomeric needle injection cap structure at one end and a rigid tubular exit member extending from the opposite end, said unitary needle injection cap and said tubular exit member being axially aligned and said tubular exit member having a barbed connector structure at its terminal end, said unitary needle injection cap having a cylindrical upper portion with a bottom surface having a circumferential channel therein, a continuous and planar top surface spaced above said circumferential channel and a compressed cylindrical portion extending downwardly adjacent said circumferential channel and wherein said unitary cylindrical injection port body has an upper portion with a plurality of securing holes therethrough, wherein said unitary elastomeric needle injection cap is aligned and secured adjacent said securing holes and within said circumferential channel, said rigid injection port body having an unobstructed funnel shaped fluid release chamber extending below said compressed cylindrical portion and perpendicularly spaced from said planar top surface of said injection cap and in communication with said tubular exit member.

13. The two piece low profile inline injection port assembly of claim 12, wherein said compressed cylindrical portion of said elastomeric needle injection cap is radially compressed approximately 5-15% and wherein said elastomer has a hardness of 30A Shore±20A Shore.

14. The two piece low profile inline injection port assembly of claim 13, wherein said unitary elastomeric needle injection cap is formed of a silicone rubber material.

15. The two piece low profile inline injection port assembly of claim 12, wherein said tubular exit member has an inner diameter smaller than the outside diameter of an injection needle.

16. The two piece low profile inline injection port assembly of claim 12, wherein an adhesive is within said circumferential channel and said securing holes and extends between said upper portion of said injection port body and said unitary injection cap.

17. The two piece low profile inline injection port assembly of claim 15, wherein said rigid cylindrical port body is constructed of a material selected from the group of materials consisting of stainless steel, titanium, PEEK, HDPE, PVC, Polystyrene, Aluminum, Polyurethane, PTFE and Acrylic.

* * * * *